United States Patent [19]
Jennings et al.

[11] Patent Number: 5,796,080
[45] Date of Patent: Aug. 18, 1998

[54] MICROWAVE APPARATUS FOR CONTROLLING POWER LEVELS IN INDIVIDUAL MULTIPLE CELLS

[75] Inventors: William Edward Jennings, Wingate; Dennis Palmer Manchester, Matthews; Edward E. King; David A. Barclay, both of Charlotte, all of N.C.

[73] Assignee: CEM Corporation, Matthews, N.C.

[21] Appl. No.: 538,745

[22] Filed: Oct. 3, 1995

[51] Int. Cl.$^6$ .............................. H05B 6/74; H05B 6/68
[52] U.S. Cl. .................. 219/697; 219/696; 219/711; 219/746; 219/751; 219/750; 422/21
[58] Field of Search .................. 219/695, 696, 219/697, 746, 763, 747, 750, 751, 710, 711; 422/21

[56] References Cited

U.S. PATENT DOCUMENTS

| | | |
|---|---|---|
| 2,562,911 | 8/1951 | Hare et al. |
| 2,704,802 | 3/1955 | Blass et al. |
| 2,909,635 | 10/1959 | Haagensen .......................... 219/748 |

(List continued on next page.)

FOREIGN PATENT DOCUMENTS

| | | |
|---|---|---|
| 0 155 893 | 9/1985 | European Pat. Off. |
| 0 156 742 | 10/1985 | European Pat. Off. |
| 0 387 161 | 9/1990 | European Pat. Off. |
| 0 434 581 | 6/1991 | European Pat. Off. |
| 0 467 625 | 1/1992 | European Pat. Off. |
| 0 468 896 | 1/1992 | European Pat. Off. |
| 0 480 857 | 4/1992 | European Pat. Off. |
| 0 496 684 | 7/1992 | European Pat. Off. |
| 0 526 626 | 2/1993 | European Pat. Off. |
| 0 549 495 | 6/1993 | European Pat. Off. |
| 0 624 051 | 11/1994 | European Pat. Off. |
| 0 661 530 | 7/1995 | European Pat. Off. |
| 2 483 970 | 12/1981 | France . |
| 2 685 478 | 1/1995 | France . |
| 2 701 112 | 4/1995 | France . |
| 41 23 921 | 1/1993 | Germany . |
| 3-129696 | 6/1991 | Japan ........................... 219/746 |
| 2 053 629 | 2/1981 | United Kingdom . |
| 2 062 428 | 5/1981 | United Kingdom . |
| WO 92/15383 | 9/1992 | WIPO . |

OTHER PUBLICATIONS

*The Kjeldahl Determination of Nitrogen: Retrospect and Prospect;* H. A. McKenzie; Trends in Analytical Chemistry, vol. 13, No. 4, pp. 138–144, 1994.

*An Application of Pressure/Temperature–Controlled Microwave Heating Curves For the Mineralization of Tuna Material Prior to Spectrometric Quantification of Mercury,* J. E. Tahan et al., Ciencia 3(2), pp. 139–148, 1995, Maracaibo, Venezuela.

*Digestione de Campioni Ambientali,* Acqua–Aria, 10, pp. 1005–1007, 1994.

*Comparison of Sample Decomposition Procedures for the Determination of Zinc in Milk by Inductively Coupled Plasma Atomic Emission Spectrometry,* A. Krushevska et al.; Journal of Analytical Atomic Spectrometry, vol. 7, Sep., 1992, pp. 851–858.

*Applications of Microwave Digestion Technique for Elemental Analyses,* H. M. Kuss; Fresenius' Journal of Analytical Chemistry, Oct., 1991, pp. 788–793.

(List continued on next page.)

*Primary Examiner*—Philip H. Leung
*Attorney, Agent, or Firm*—Philip S. Summa, Patent Attorney

[57] ABSTRACT

A microwave processing system is disclosed. The system is particularly useful for concurrently controlling a plurality of chemical reactions from a single microwave source. The system comprises a source that produces electromagnetic radiation in the microwave range; a waveguide in communication with the source and into which the source propagates microwave radiation; a resonator in communication with the waveguide; and an adjustable dynamic moderating device between the waveguide and the resonator for moderating the wave energy passing from the waveguide to the resonator without substantially changing the propagated mode in the waveguide.

13 Claims, 5 Drawing Sheets

U.S. PATENT DOCUMENTS

| | | |
|---|---|---|
| 3,471,672 | 10/1969 | White . |
| 3,545,093 | 12/1970 | Forster . |
| 3,560,695 | 2/1971 | Williams et al. . |
| 3,570,391 | 3/1971 | Rejler . |
| 3,665,142 | 5/1972 | Johnson . |
| 3,723,900 | 3/1973 | Johnson . |
| 3,739,130 | 6/1973 | White . |
| 3,806,689 | 4/1974 | Kegereis et al. . |
| 3,851,131 | 11/1974 | Johnston et al. . |
| 3,880,586 | 4/1975 | Murayama et al. . |
| 3,916,137 | 10/1975 | Jurgensen . |
| 4,027,133 | 5/1977 | Dygve et al. . |
| 4,163,140 | 7/1979 | Bardet . |
| 4,191,876 | 3/1980 | Ohkubo et al. . |
| 4,193,027 | 3/1980 | Wyslouzil . |
| 4,210,793 | 7/1980 | Fournet-Fayas . |
| 4,245,143 | 1/1981 | Miura et al. . |
| 4,286,134 | 8/1981 | Nakata et al. . |
| 4,314,128 | 2/1982 | Chitre . |
| 4,324,965 | 4/1982 | Naumann et al. . |
| 4,347,216 | 8/1982 | Kawasaki et al. . |
| 4,374,216 | 2/1983 | Dammann . |
| 4,444,723 | 4/1984 | Matsumaru et al. . |
| 4,461,941 | 7/1984 | Fukuda et al. . |
| 4,499,357 | 2/1985 | Kojima . |
| 4,517,430 | 5/1985 | Slottag . |
| 4,568,199 | 2/1986 | Schmidt . |
| 4,617,440 | 10/1986 | Gics . |
| 4,681,740 | 7/1987 | Commarmot et al. . |
| 4,693,867 | 9/1987 | Commarmot et al. . |
| 4,714,810 | 12/1987 | Sirkis . |
| 4,714,812 | 12/1987 | Haagensen et al. . |
| 4,734,553 | 3/1988 | Noda . |
| 4,751,356 | 6/1988 | Fukuda et al. . |
| 4,922,180 | 5/1990 | Saffer et al. . |
| 5,006,785 | 4/1991 | Revus et al. . |
| 5,059,400 | 10/1991 | Bénézech et al. . |
| 5,068,086 | 11/1991 | Sklenak et al. . |
| 5,099,096 | 3/1992 | Kimrey, Jr. et al. . |
| 5,103,181 | 4/1992 | Gaisford et al. . |
| 5,191,182 | 3/1993 | Gelorme et al. . |
| 5,205,050 | 4/1993 | Masaaki et al. . |
| 5,304,766 | 4/1994 | Baudet et al. . |
| 5,308,944 | 5/1994 | Stone-Elander et al. . |
| 5,365,043 | 11/1994 | Bradford . |
| 5,369,250 | 11/1994 | Meredith . |
| 5,393,492 | 2/1995 | Di Martino et al. . |
| 5,400,524 | 3/1995 | Leconte et al. . |
| 5,403,747 | 4/1995 | Akins, Jr. et al. . |
| 5,420,401 | 5/1995 | Jacquault et al. . |
| 5,459,302 | 10/1995 | Jacqualt . |
| 5,468,940 | 11/1995 | Kang ......................................... 219/746 |
| 5,512,736 | 4/1996 | Kang et al. ............................... 219/750 |

OTHER PUBLICATIONS

*Development of Inorganic Microwave Dissolutions*, B. D. Zehr, American Laboratory, Dec. 1992, pp. 24–29.

*Definition of Reference Procedures for Focused Microwave Digestion*, M. H. Feinberg, Analysis (1991) 19, pp. 47–55.

*Mineralisation Voie Humide Au Moyen d'une Source Micro–ondes*, D. Didenot, Technologie Appliquee, pp. 44–50.

*Present Status of Microwave Sample Dissolution and Decomposition for Elemental Analysis*, H. Matusiewicz et al.; Prog. Analyt. Spectrosc. vol. 12, 1989, pp. 21–39.

*Comparison of Four Methods for Digesting Food Samples for Determination of Trace Levels of Cadmium by Flameless Atomic Absorption Spectrophotometry*, M. T. Cabanis et al., J. Assoc. Off. Anal. Chem., vol. 71, No. 5, (1988) pp. 1033–1037.

*Fundamental Relationships in Acid Decomposition of Samples for Elemental Analysis Using Microwave Energy*, H. M. Kingston et al.; Met. Res. Soc. Symp. Proc. vol. 124, 1988, pp. 121–134.

*Method Performance –More Powerful Peroxide Kjeldahl Digestion Methods*, C. C. Hach et al.; J. Assoc. Off. Anal. Chem., vol. 70, No. 5, 1987, pp. 783–787.

*Mineralizace Organickych Latek Pro Stanoveni Rtuti*, J. Pikhart et al., Chemicky Prumysi roc. 29/54 (1979) pp. 310–313.

*The Kjeldahl Determination of Nitrogen: A Critical Study of Digestion Conditions–Temperature, Catalyst, and Oxidizing Agent*, H. A. McKenzie et al., Australian Journal of Chemistry, vol. 7, Melbourne, 1954, pp. 55–70.

*Determination of Total Mercury by Microwave Digestion*, K. W. Panaro, Laboratory Information Bulletin, Boston District, No. 2525, 1981, pp. 1–9.

*Industrial Microwave Heating*, Hazards, Leakage and Safety, A. C. Metaxas et al., Chapter 10, pp. 282–286, 1983.

*Measurement of the Complex Permittivity of Food Products During Microwave Power Heating Cycles*, C. Akyel et al., Journal of Microwave Power, 18(4), 1983, pp. 355–365.

*Microwave Apparatus for Controlled Heating of Aqueous Solutions*, C. De Wagter et al., International Microwave Power Institute, 19th Annual Meeting, 1984, Minneapolis, MN, pp. 196–199.

*Microwave Heating*, Microwave Containment, D. A. Copson, The AVI Publishing Co., 2nd Ed., 1975, pp. 126–131.

*Microwave Heating In Freeze–Drying, Electronic Ovens, and Other Applications*, D. A. Copson, The AVI Publishing Co., Inc., 1962, pp. 114–135.

*Microwave Oven Digestions*, R. C. Williams, Youngstown State University, Spring 1990.

*Microwave Oven–Based Wet Digestion Technique*, P. Barrett et al., American Chemical Society, 1978, pp. 1021–1023.

*Microwave Processing of Tree Seeds*, S. C. Kashyap et al., Journal of Microwave Power, 9(2) 1974, pp. 99–107.

*Temperature Controlled Microwave Oven Digestion System*, D. W. Mincey et al., Analysis Chimica Acta, 264, pp. 97–100, 1992.

*Temperature Controlled Microwave Oven Digestion System*, R. Williams et al., Youngstown State University, Youngstown, OH.

*A Multichannel Infrared Fiberoptic Radiometer for Controlled Microwave Heating*, S. Drizlikh et al., SPIE vol. 1201 Optical Fibers in Medicine V (1990) pp. 353–359.

*Microwave Dissolutions*, Focus.

International Search Report, PCT/US 96/14530; Filed Nov. 9, 1996; by A. Hocquet mailed 10 Jan., 1997.

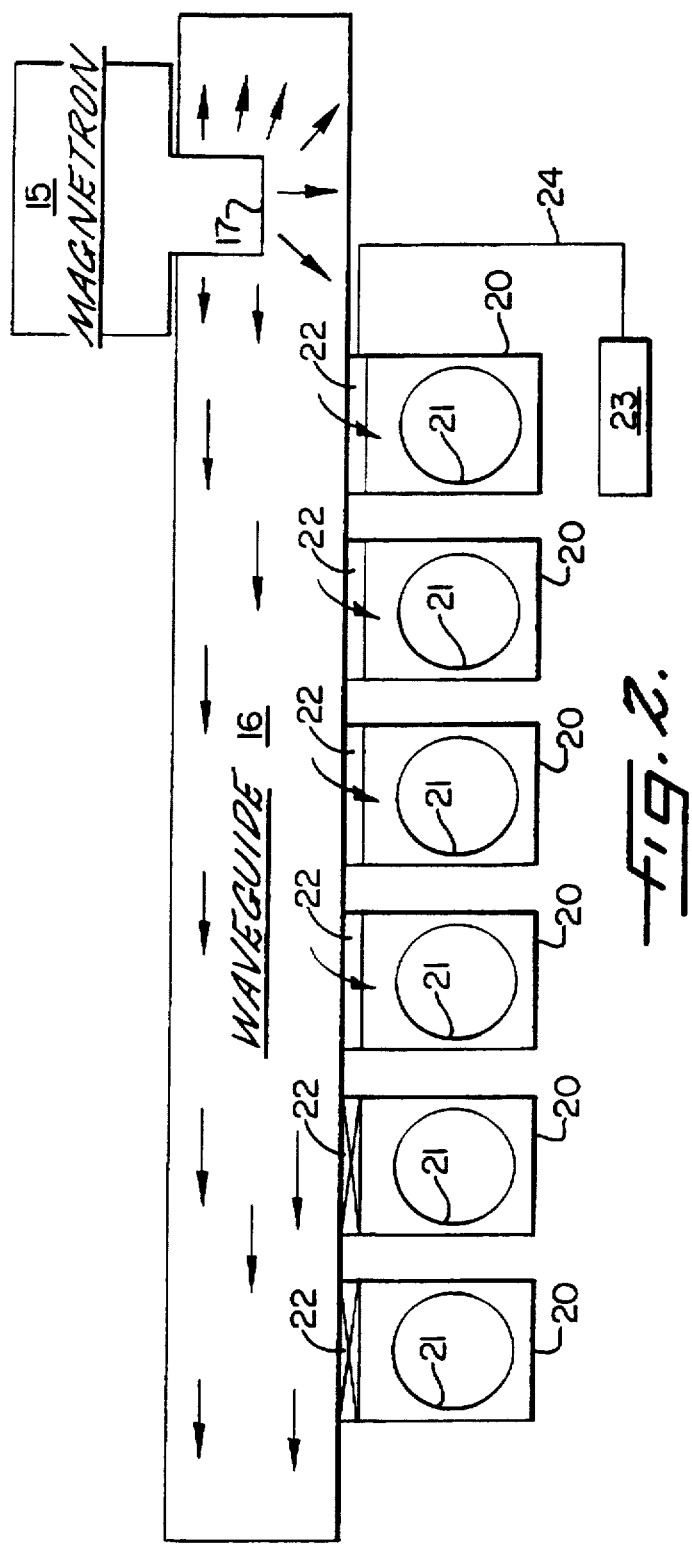

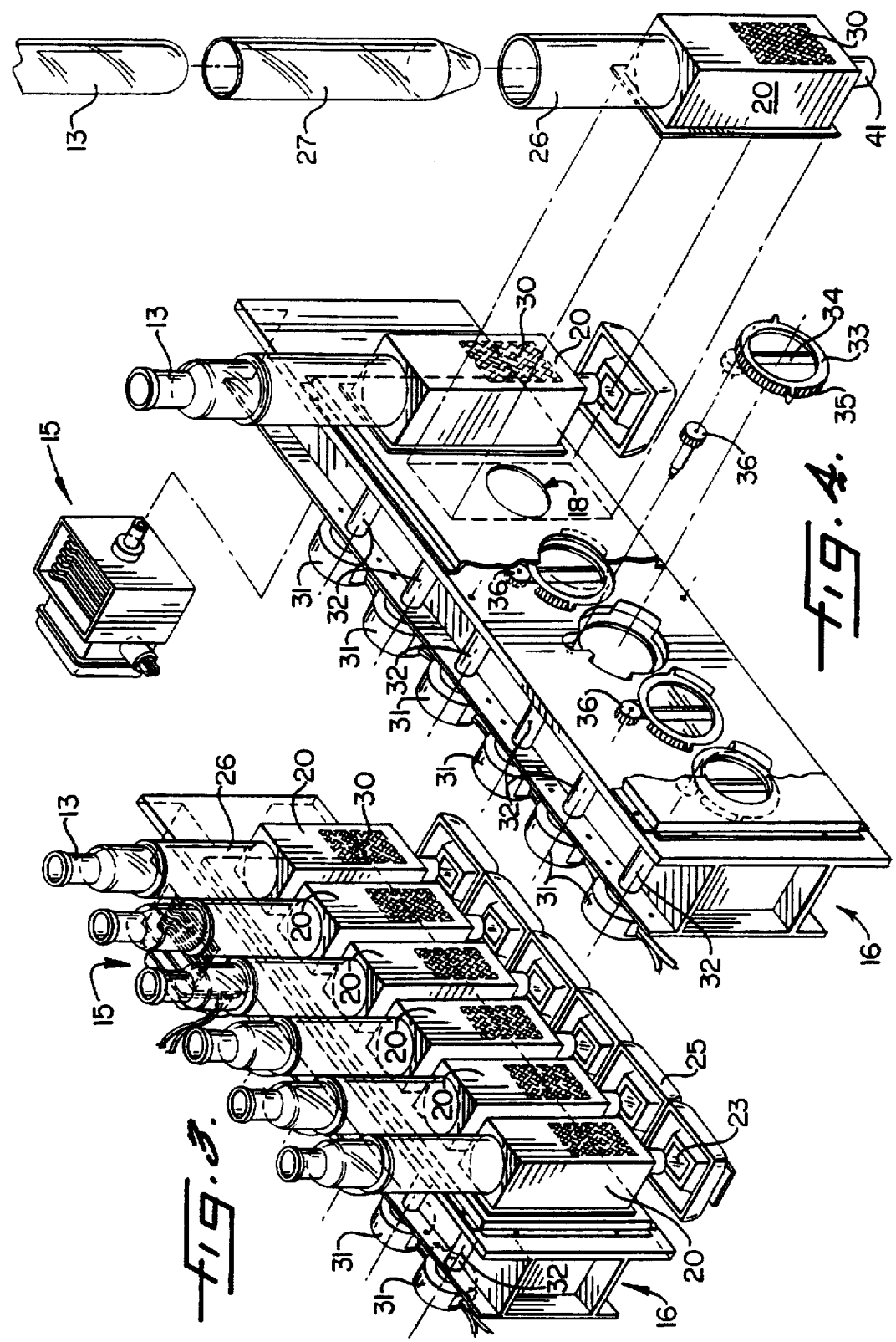

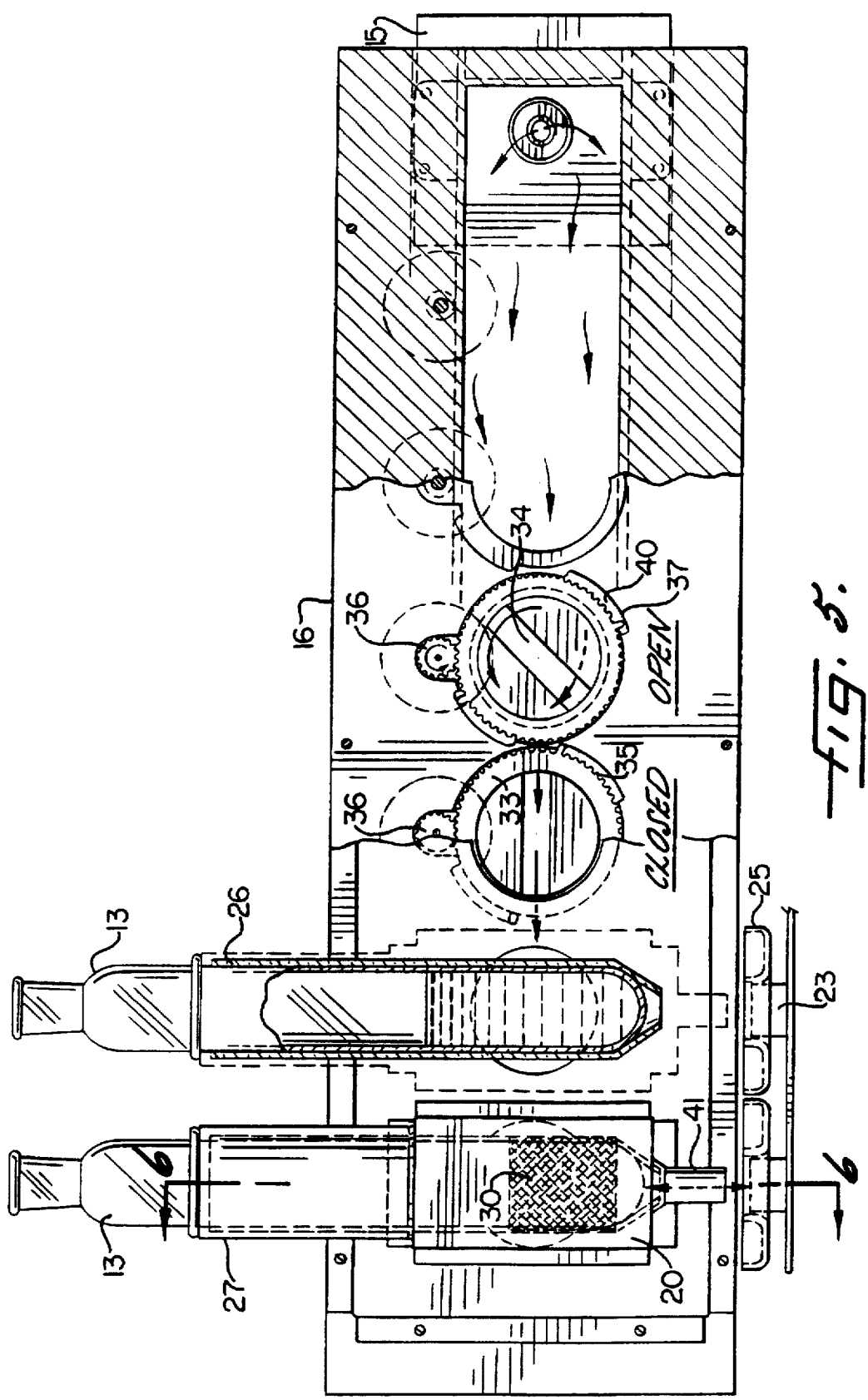

MICROWAVE APPARATUS FOR CONTROLLING POWER LEVELS IN INDIVIDUAL MULTIPLE CELLS

The present invention relates to an apparatus for microwave processing of laboratory-type samples, and in particular relates to an apparatus for individually controlling and processing a plurality of microwave responsive samples using a single magnetron, and for carrying out associated microwave assisted chemical reactions. This application is related to Ser. No. 08/538,603 filed concurrently herewith for "Microwave Assisted Chemical Processes," and which is incorporated entirely herein by reference.

BACKGROUND OF THE INVENTION

"Microwave" is the term used to describe the portion of the electromagnetic spectrum that has wavelengths ($\lambda$) between the far infrared and the radio frequency; i.e. between about one millimeter (mm) and about 30 centimeters (cm), with corresponding frequencies (v) in the range from about 1 to 300 gigahertz (GHz). The upper and lower limits of the range defined as "microwave" are, of course, somewhat arbitrary. Microwave radiation has a number of useful purposes, including spectroscopy, communication, navigation, and medicine, but one of the most common uses is as a heating medium, particularly for food; i.e. the almost ubiquitous "microwave oven."

Because microwaves are useful for heating substances that respond to these frequencies of electromagnetic radiation (i.e., those with a high dielectric absorption, "loss tangent", or "loss factor"), use of microwave power to heat chemical reagents and drive chemical reactions other than food preparation has greatly increased over the last several decades. As well known to chemists and those in related fields, most chemical reactions either require or benefit from the application of heat. For several generations of chemists, heating has typically been done with the classic bunsen burner, or more recently heated plates ("hot plates"). Nevertheless, the use of microwave energy is entirely appropriate, if all other factors are likewise conducive to the use of microwaves.

Accordingly, there are a number of commercially available microwave devices (generally analogous to microwave ovens that are designed for laboratory use.

A typical microwave device for laboratory heating (sometimes referred to as "microwave assisted" chemistry) uses a magnetron as the microwave source, a waveguide (typically a hollow circular or rectangular metal tube of uniform cross section) to guide the microwaves, and a resonator (sometimes also referred to as the "cavity") into which the microwaves are directed to heat a sample. A magnetron is not the only potential source of microwave radiation. Klystrons, travelling wave tubes, oscillators, and certain semiconductor devices can also produce microwaves. Magnetrons are, however, simple and economical from a number of standpoints and thus are widely used in microwave devices for both home and laboratory. One disadvantage of magnetrons, however, is that they produce a single frequency (i.e. a narrow band) at a given power level. Thus, when attempting to adjust the power to be directed towards a sample in a resonator, the most common method of controlling the magnetron is to run it at its designated power while turning it on and off on a cyclical basis.

For example, when a typical magnetron-source microwave device is set to run at 50 percent power, in reality the magnetron runs at full power for 50 percent of the time on a cyclical basis.

When microwave devices are used for chemical reactions, a common technique for maximizing their efficiency is to run a plurality of reactions in separate containers ("vessels") at the same time in a single, relatively large resonator. The containers are typically made of a microwave transparent material such as an appropriate glass, plastic, or ceramic. Generally, a plurality of two or more containers, and sometimes as many as fifty (50), are placed in the cavity of a laboratory microwave device and then radiated with the microwaves. In a typical circumstance, one of the vessels is monitored for pressure, temperature, color change, or some other parameter that measures or indicates the progress of the reaction in that single vessel. The remaining unmonitored vessels are considered to have behaved identically to the monitored vessel. This is, however, only a best estimate, as is recognized by those of ordinary skill in this art.

Although every single vessel in a single resonator could be individually monitored, the complexity of doing so would greatly reduce efficiency and raise costs undesirably. Furthermore, because most devices use a single magnetron as the source, individual monitoring would still lack individual control.

Such single monitoring systems, however, have a number of weaknesses. Primarily, the wavelengths of microwaves are small enough (a 2.45 Ghz magnetron produces a 12.25 cm wavelength) that in a cavity the size of a typical home microwave oven or laboratory microwave device, the microwaves will reflect and interfere with one another at a plurality of locations in a manner well understood by those familiar with wave propagation. As a result, the typical cavity is full of standing waves that define a number of nodes (i.e. high energy interference points) and nulls (low energy interference points).

As a point of definition, the term "node" generally (and as used herein) refers to a high energy point in a wave interference pattern. The phonetically similar term "model", however, refers to the wave pattern itself in a defined area such as the resonator of a microwave device. Accordingly, microwaves in a resonator can produce a "mode" within the resonator that in turn includes a plurality of nodes and nulls.

Accordingly, in the absence of any other factors, the cavity of a typical microwave device will tend to produce a number of hot and cool spots in the items in the cavity. In order to alleviate this condition, the microwaves exiting the magnetron and the waveguide are typically "stirred" by a rotating reflector very similar to an ordinary electric fan. The stirrer changes the pattern of microwaves into a number of continuously differing patterns so that the instantaneous position of nodes and nulls is constantly changing, thus bringing some degree of uniformity to (or at least reducing the discontinuities in) the energy distribution in the cavity.

As another factor, however, the presence of samples and sample containers in a microwave oven also changes the interference pattern within the cavity. Thus, even if the interference pattern of a given microwave cavity could be predicted, placing an object, sample container, or chemical sample in the oven to be heated would immediately change the interference pattern.

Accordingly, a fundamental problem remains: if multiple samples are treated with microwaves from a single magnetron source, that treatment will (1) be less than uniform; and (2) lack individual control. Thus, where the chemical reaction task at hand is to treat a plurality of samples, the lack of uniformity is a recognized problem in typical laboratory microwave devices. In other circumstances, where individual reactions, whether of the same or different reagents, must be individually controlled, the typical microwave device is similarly less useful, less efficient, or even useless.

As mentioned above, sources other than magnetrons can be used to produce microwaves, and indeed to control the power level from microwaves, but such sources are somewhat more complex and in many purposes more expensive than the magnetron.

Accordingly, the need exists for a microwave apparatus for driving chemical reactions that can control multiple samples at different power levels from a single magnetron and that can individually adjust the power level to the individual samples as needed or desired.

OBJECT AND SUMMARY OF THE INVENTION

It is therefore an object of the present invention to provide a microwave processing system that is particularly useful for concurrently controlling a plurality of chemical reactions from a single microwave source.

The invention meets these and other objects with a microwave processing system that comprises a source that produces electromagnetic radiation in the microwave range, a waveguide in communication with the source and into which the source propagates microwave radiation, a resonator in communication with the waveguide, and adjustable dynamic moderating means between the waveguide and the resonator for moderating the wave energy passing from the waveguide to the resonator without substantially changing the propagated mode in the waveguide.

The foregoing and other objects, advantages and features of the invention, and the manner in which the same are accomplished, will become more readily apparent upon consideration of the following detailed description of the invention taken in conjunction with the accompanying drawings, which illustrate preferred and exemplary embodiments, and wherein:

DESCRIPTION OF THE DRAWINGS

FIG. 2 is a schematic diagram of the relationship between the magnetron, waveguide, adjustable moderating means and resonators of the present invention;

FIG. 3 is a perspective view of the magnetron, waveguide and resonator portions of the invention, along with typical sample containers and the monitoring devices of the present invention;

FIG. 4 is a partial and partially exploded view of FIG. 3 and showing some of the elements thereof in greater detail;

FIG. 5 is a front elevational view, partially broken away, of one embodiment of the invention.

DETAILED DESCRIPTION

Figure 1:
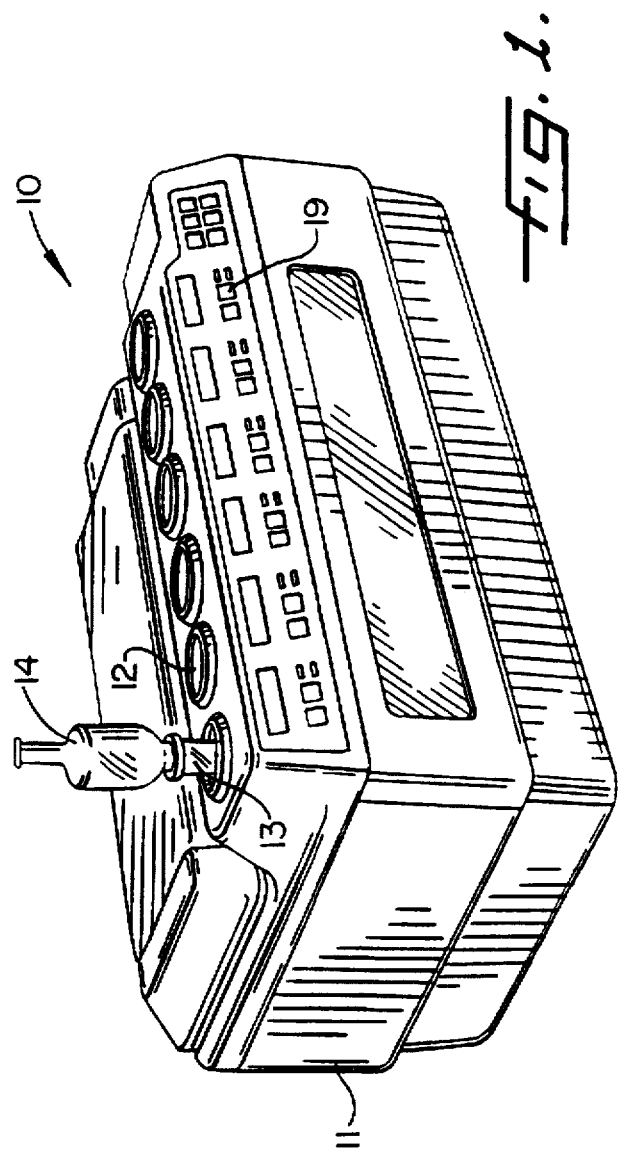
FIG. 1 is a perspective view of a commercial embodiment of the present invention.

FIG. 1 is a perspective rendering of a commercial embodiment of the present invention generally designated at 10. FIG. 1 illustrates the invention in a commercial housing 11, and thus a number of details will be explained with reference to FIGS. 2–6 rather than with respect to FIG. 1. FIG. 1 does illustrate, however, a plurality of reaction cells 12, which as explained in more detail herein, are the resonators of the microwave processing system according to the invention.

FIG. 1 also illustrates that when chemical reactions are carried out in the microwave processing system 10, they are usually done in a container of some sort illustrated in FIG. 1 as a glass reaction vessel 13 with a cold trap, vent, or reflux apparatus 14 on top of the reaction vessel 13 to control the reaction by-products (often gases) in any desired fashion.

FIG. 1 also illustrates that the invention provides individual controls 19 for each of the reaction cells 12, and the ability to control the cells individually while using a single waveguide and a single magnetron is one of the primary useful features of the present invention.

The operating details of the invention are best illustrated by FIGS. 2–6.

FIG. 2 illustrates the main features of the invention in schematic fashion. As illustrated therein, the microwave processing system comprises a microwave source shown as the magnetron 15 that produces electromagnetic radiation in the microwave range. The microwave source 15 can be any appropriate source, some of which include klystrons, travelling wave tubes, various electronic oscillators, and solid state sources including various transistors and diodes. As will become apparent herein, however, one of the particular advantages of the invention is that a single magnetron, which typically is a less expensive and simpler device for producing the appropriate microwave radiation, can be used at a single frequency and at a given or selected power level while individually controlling a plurality of different chemical reactions.

In this regard, the basic theory and operation of microwave devices and the like are relatively well known and will not be explained in detail herein other than as necessary to describe the claimed invention. A number of straightforward discussions are available from common sources, however, including for example the *McGraw Hill Encyclopedia of Science and Technology*, 7th Edition (1992) starting at page 159 of Volume 11.

Similarly, a good explanation of solid state devices and the theory of their operation and microwave capabilities are given in Sze, *Physics of Semiconductor Devices*, 2nd Edition (1981) and particularly in chapters 9, 10 and 11 covering pages 513–678.

FIG. 2 further illustrates that the magnetron 15 is in communication with a waveguide 16 into which the magnetron 15 propagates microwave radiation through the antenna 17.

At least one, and preferably a plurality of resonators 20 are in communication with the waveguide 16. FIG. 2 illustrates that the resonators 20 include circular sample holders 21, it being understood that neither the invention nor the vessels are limited to this shape, but that the circular shape is typically the most convenient for reaction vessels for chemical reactions.

FIG. 2 illustrates a microwave processing system with six resonators, but it will be understood that the invention is not limited to any particular number of resonators, and that a system with a single resonator can comprise one embodiment of the present invention as can a system with two or more resonators.

FIG. 2 further illustrates in schematic fashion the adjustable dynamic moderating means 22 between the waveguide 16 and the resonators 20 for moderating the wave energy passing from the waveguide to the resonator without substantially changing the propagated mode in the waveguide.

As used herein, the term "dynamic" is applied in its sense of describing force related to motion, and as the opposite of "static". Stated somewhat differently, the adjustable dynamic moderating means 22 moves to adjustably control the passage of microwaves while the microwaves are passing from the waveguide to the resonator.

As noted earlier, the cross-sectional dimensions of a waveguide such as the waveguide 16 determine a frequency and a corresponding wavelength below which transmission becomes minimal or nonexistent. This is referred to as the "cutoff" frequency or wavelength. In a waveguide, the mode with the lowest cutoff frequency is called the "dominant" mode. As further noted above, placing samples in a typical waveguide or resonator tends to change the pattern of electromagnetic field components and thus change the modes in an uncontrolled manner.

In contrast, in the present invention the waveguide remains the same, and the propagated modes (nodes and nulls) remain substantially the same therein, even while the individual resonators are being individually controlled.

As further schematically illustrated in FIG. 2, the invention includes means, shown as the infrared pyrometer 23, for monitoring the effects of microwaves on a sample in the resonator 20 and means, shown as the feedback loop 24, in communication with the monitoring means 23 and the adjustable moderating means 22, for controlling the moderating means 22 based upon the effects of microwave energy on the sample in the resonator 20 monitored by the monitoring means 23.

A number of appropriate control systems can be used to control the moderating means 22 based on input from the pyrometer 23, and these are well known to those of ordinary skill in these arts. By way of example and not limitation, however, various control systems are described in appropriate fashion in R. Dorf, *The Electrical Engineering Handbook*, 1993, CRC Press, Inc., pages 2099–2153.

As known to those familiar with monitoring chemical reactions, an infrared pyrometer measures the temperature of a reaction (or of a vessel heated by a reaction, or both) by monitoring the infrared radiation emitted by the reaction. The invention is not limited to infrared pyrometers, however, because depending upon the type of chemical reaction taking place, any other appropriate monitoring device or parameter could be used. These could include color within the visible spectrum, electromagnetic radiation from some other part of the spectrum (for example ultraviolet radiation), or the measurement of gas pressure or volume generated, or any other parameter appropriate to the particular chemical reaction being monitored and to the monitoring device being used. In general, however, an infrared pyrometer is noninvasive and thus convenient for many laboratory applications.

FIGS. 3 and 4 illustrate the present invention in more detail and for the sake of consistency with FIG. 1, the magnetron is broadly designated as 15 in FIGS. 3 and 4, the waveguide as 16, and the ports as the circular openings 18.

In addition to illustrating the magnetron 15, the waveguide 16, and six resonators 20, FIG. 3 also illustrates a respective pyrometer 23 for each respective resonator 20. In the embodiment illustrated in FIG. 3, the pyrometer further includes a small spill tray 25 that protects it from any accidental overflow of reagents from the reaction vessels.

In the illustrated embodiment, the waveguide 16 has a rectangular cross-section, and is formed of an appropriate metal that will reflect, and thus direct, the microwaves within the waveguide 16.

FIG. 3 further illustrates that in typical embodiments, the chemical reactions generally will be carried out in cylindrical vessels 13 (as also illustrated in FIG. 1) and which are maintained in position by the upright holders 26 and in preferred embodiments an additional sleeve 27 (FIG. 4). FIG. 3 also illustrates that the resonators 20, which are also formed of metal, include partially covered openings 30 that can be used to permit a visual inspection of reactions taking place in the vessels 13, and which are covered by an appropriate medium, such as a metal screen or other conductive material, that prevents microwaves from escaping from the resonator 20 through the opening 30.

FIG. 3 also illustrates that each resonator 20 has a respective associated motor 31 and shaft 32 that form part of the moderating means 22 (FIG. 2) in a manner to be described herein.

FIG. 4 illustrates that the adjustable moderating means 22 (FIG. 2) comprises a port 18 between the waveguide 16 and the resonator 20 for permitting microwave radiation to communicate between the waveguide 16 and the resonator 20. As used herein, and in microwave terminology in general, the term "port" describes an opening through which microwaves can pass. The port has an aperture used in conjunction with adjusting means which can change the amount of microwave radiation that reaches the resonator 20 from the waveguide 16. The aperture includes the rotating cover disk 33 over the port 18 between the waveguide 16 and the resonator 20. The cover disk 33 includes a slot 34. The aperture disk 33 and the slot 34 are adjustable through a range of positions in which the aperture will pass, partially pass or block microwave radiation. In general, the size and shape of the slot can be selected on the basis of the dominant frequency produced by the magnetron and the waveguide, and the orientation affects the extent to which the electric field vector is transmitted through it. From a functional standpoint, the slot should be wide enough to avoid heating the slot as the energy passes through, while narrow enough to block the microwaves when the slot is rotated. In the illustrated embodiment, the magnetron produces 2.455 GHz and the slot's dimensions are about 6 cm long by 1.2 cm wide.

It will be understood that the disk and slot system illustrated and described herein are illustrative of the moderating means of the present invention rather than limiting of it. Other dynamic systems could include (but are similarly not limited to) various wire arrangements across the port, or the use of an electromagnet to vary the field, and thus the energy, passing through the port to the resonator. It will be understood that such an electromagnet would function dynamically even though it would lack moving parts.

The disk 33 has a plurality of teeth 35 on its circumference. In a preferred embodiment the teeth 35 are formed of plastic to avoid the necessity for additional grounding. Metal teeth can be used if properly grounded. The microwave processing system additionally comprises a gear 36 for which the motor 31 and shaft 32 provide driving means to thereby rotate the disk, change the orientation of the slot 34 in the port 18, and thereby change the amount of microwave radiation that reaches the resonator from the waveguide.

In this regard, the position of each of the resonators 20 with respect to the waveguide 16 is based upon the wavelength produced by the magnetron 15 and the null and node positions that are defined by the waveguide 16 at the wavelength produced by the magnetron 15. Most preferably, the waveguide 16 comprises a single mode waveguide that can be designated as a $TE_{10x}$ waveguide in microwave terminology, where x designates the number of nulls in the propagated direction.

As shown schematically in FIG. 2, the pyrometer 23 and the feedback loop or circuit 24 are in electrical communication with the motor 31 so that the degree to which the motor rotates the disk 33—and therefore the slot 34—is controlled by the temperature measurement from the pyrometer 23.

Furthermore, the degree to which the slots pass or block microwaves is substantially proportional to the degree of rotation of the slot, thus providing a far more accurate proportionate temperature control than the typical technique of interrupting the magnetron's full power on a cyclical basis. Additionally because of the individual temperature monitoring and individual slot control, any one or more (or all) of the slot positions can be optimized regardless of the number of other slots that are either open or closed.

In accordance with the present invention, it has been found that if the waveguide 16 and the position of the ports 18 are properly coordinated, relatively small movements of the slot 34 can change the degree to which microwave energy reaches the resonator from the waveguide from complete blockage to complete communication, and with a number of partial transmissions in between. Using the embodiment illustrated in FIGS. 3 and 4, a rotation of the disk 33 and slot 34 over a range of between about 0° and 90°, and preferably between about 0° and 45°, is sufficient to concurrently provide each individual resonator 20 with any degree of desired microwave energy from the waveguide 16, and yet without substantially changing the propagated mode in the waveguide.

FIG. 5 is a side elevational view showing a number of the same elements and likewise illustrating that the shape and position of the slot 34 are such that a 45° rotation of the slot 34 will either open or close the slot to microwave transmission. FIG. 5 also illustrates that the rotation of the disk 33 is limited by a finger 37 that moves in a channel 40 to help control and limit the degree to which the slot can be rotated. In the embodiment illustrated in FIG. 5, the aperture is closed to microwaves when the slot is horizontally oriented, and fully open to microwaves when the slot is approximately 45° from vertical. It will be understood that the particular opened and closed positions for a particular slot will depend upon the size and shape of the waveguide and resonator, but can be easily determined on a case-by-case basis without undue experimentation.

Figure 6:
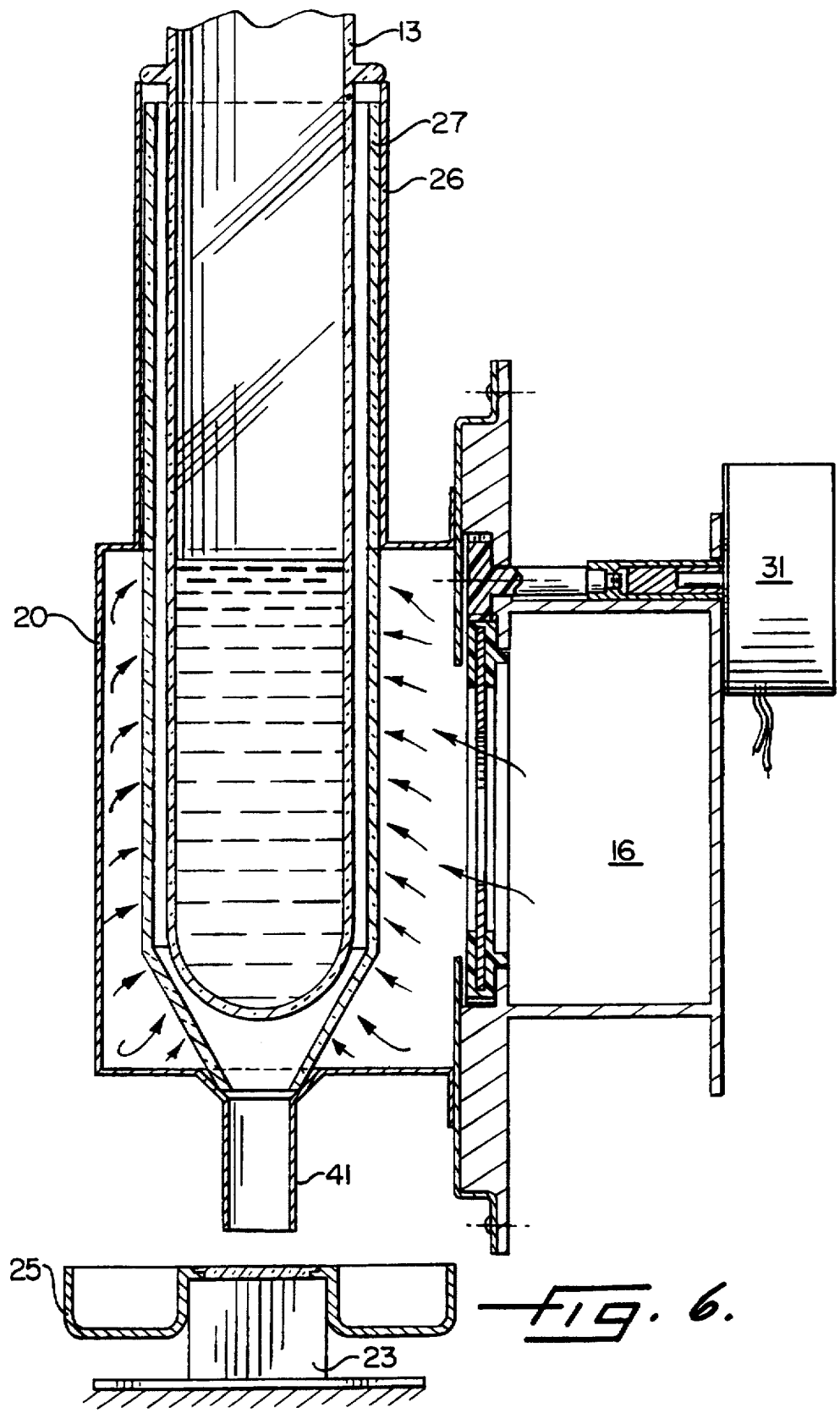
FIG. 6 is a cross-sectional view taken along line 6—6 of FIG. 5.

FIG. 6 shows a single cell and resonator in somewhat more detail, and illustrates that the resonator 20 has a measurement access opening shown as the tube-like member 41 extending from its lowest portion to permit the reaction taking place in the vessel 13 to be appropriately monitored. As noted above, neither the position of the pyrometer 23, nor its specific function as a temperature measurement device are limiting of the claimed invention, but simply represent a convenient method of monitoring a chemical reaction under many circumstances particularly one carried out at elevated temperatures.

In the drawings and specification, there have been disclosed typical preferred embodiments of the invention and, although specific terms have been employed, they have been used in a generic and descriptive sense only and not for purposes of limitation, the scope of the invention being set forth in the following claims.

That which is claimed is:

1. A microwave processing system that is particularly useful for concurrently controlling a plurality of chemical reactions from a single microwave source, said system comprising:

a microwave source for producing electromagnetic radiation in the microwave range;

a waveguide in communication with said microwave source and into which said microwave source propagates microwave radiation that includes a dominant mode in said waveguide;

a plurality of individual and separate resonators in communication with said waveguide; and a plurality of adjustable dynamic moderating means with one of said respective adjustable dynamic moderating means between each said resonator and said waveguide for adjustably moderating the wave energy passing from said waveguide to each said resonator independent of said remaining resonators, without affecting the wave energy transmitted to said remaining resonators and without substantially changing the propagated dominant mode of microwave radiation in said wave guide.

2. A microwave processing system according to claim 1 wherein said microwave source is selected from the group consisting of klystrons, electronic oscillators, travelling wave tubes, transistors, and diodes.

3. A microwave processing system according to claim 1 wherein the position of each said resonator with respect to said waveguide is based upon the wavelength produced by said microwave source and the null and mode positions that are defined by said waveguide at the wavelength produced by said microwave source.

4. A microwave processing system according to claim 1 comprising two separate resonators in independent communication with said waveguide.

5. A microwave processing system according to claim 1 comprising six separate resonators in independent communication with said waveguide.

6. A microwave processing system according to claim 1 wherein said waveguide comprises a single mode waveguide.

7. A microwave processing system according to claim 1 and further comprising:

means for independently monitoring the effects of microwaves on a sample in each of said resonator; and means in communication with said monitoring means and said adjustable moderating means for controlling said moderating means based upon the effects of microwave energy on the sample in said resonator monitored by said monitoring means.

8. A microwave, processing system according to claim 7 wherein said monitoring means comprises means for measuring the temperature of a sample in a resonator.

9. A microwave processing system according to claim 8 wherein said temperature measuring means comprises a pyrometer.

10. A microwave processing system according to claim 7 wherein said adjustable moderating means comprises:

a respective port between said waveguide and each said resonator for permitting microwave radiation to communicate between said waveguide and each of said resonators;

an aperture in said port that is adjustable between positions in which the aperture will pass, partially pass, or block microwave radiation; and means for adjusting said aperture to thereby change the amount of microwave radiation that reaches said resonator from said waveguide.

11. A microwave processing system according to claim 10 wherein said aperture comprises:

a rotating disk over said port between said waveguide and said resonator said disk having a plurality of teeth on the circumference of said disk;

a gear in engagement with at least some of said teeth; and a motor for driving said gear to thereby rotate said disk, change the orientation of said opening and thereby change the amount of microwave radiation that reaches said resonator from said waveguide; and a slot in said moveable cover.

12. A microwave processing system according to claim 11 wherein said slot is wide enough to avoid becoming overheated by microwaves passing therethrough, while small enough to block the passage of microwaves when the slot is rotated.

13. A microwave processing system according to claim 11 wherein said monitoring means comprises a pyrometer and said communication means comprises a feedback circuit between said pyrometer and said motor for controlling said motor and said aperture, and thereby controlling the microwave energy reaching the sample based upon the input from the pyrometer and thus based upon the temperature of the sample.

* * * * *